US00PP08890P

United States Patent [19]

VandenBerg

[11] Patent Number: Plant 8,890

[45] Date of Patent: Sep. 13, 1994

[54] CARNATION PLANT NAMED ADELA

[75] Inventor: Cornelis P. VandenBerg, Salinas, Calif.

[73] Assignee: Yoder Brothers, Inc., Barberton, Ohio

[21] Appl. No.: 99,660

[22] Filed: Jul. 30, 1993

[51] Int. Cl.[5] ..... A01H 5/00
[52] U.S. Cl. ..... Plt./70.3
[58] Field of Search ..... Plt. 70.3

*Primary Examiner*—James R. Feyrer
*Attorney, Agent, or Firm*—Foley & Lardner

[57] ABSTRACT

A carnation plant named Adela particularly characterized by its commercial double flower type; flat, high centered flower form; white flower color; diameter of flower 65 to 70 mm when fully opened, when grown as a spray carnation; petal margins are strongly serrated, with shallow to intermediate serration; strong, flexible stems; high production of flowers, with 5 to 6 flowering laterals developing per stem; flowering response of 26 to 30 weeks after planting rooted cuttings; very low incidence of splitting of calyx; very resistant to *Fusarium oxysporum;* and recommended as a miniature (spray) carnation.

2 Drawing Sheets

The present invention comprises a new and distinct cultivar of carnation, botanically known as *Dianthus caryophyllus L.* and referred to by the cultivar name Adela.

Adela, identified as 2192 (85-034006), was originated from a cross made under supervision of Cornelis P. VandenBerg in a controlled breeding program in Salinas, Calif., in 1984.

The female parent of Adela was the cultivar identified as Jolivette, a yellow spray carnation.

The male parent of Adela was an unnamed seedling, identified as 82-501-003, and described as a pink spray carnation.

The breeding program resulting in Adela has as its objective the creation of new carnation cultivars resistant to *Fusarium oxysporum.* In order to ensure resistance, seedlings were planted in a controlled environment in soil heavily infested with *Fusarium oxysporum* in Suba near Bogota, Colombia, South America. Seedlings were allowed to grow for 18 months, with removal of those seedlings that died from *Fusarium oxysporum.*

Adela was discovered and selected as one flowering plant within the progeny of the stated cross by Cornelis P. VandenBerg in October 1986, in the above desired location.

The first act of asexual reproduction of Adela was accomplished when vegetative cuttings were taken from the initial selection in Suba, Colombia in October 1986, immediately after selection, by technicians working under the supervision of Cornelis P. VandenBerg.

Horticultural examination of controlled flowerings of successive plantings has shown that the unique combination of characteristics as herein disclosed for Adela are firmly fixed and are retained through successive generations of asexual reproduction.

Adela has not been observed under all possible environmental conditions. The phenotype may vary significantly with variations in environment such as temperature, light intensity and daylength, without, however, any variance in genotype.

The following observations, measurements and comparisons describe plants grown in Suba near Bogota, Colombia, under greenhouse conditions which approximate those generally used in commercial greenhouse practice.

The following traits have been repeatedly observed and are determined to be basic characteristics of Adela, which, in combination, distinguish this carnation as a new and distinct cultivar:

1. Commercial double flower type.
2. Flat, high centered flower form.
3. White flower color.
4. Diameter of flower of 65 to 70 mm when fully opened, when grown as a spray carnation.
5. Petal margins are strongly serrated, with shallow to intermediate serration.
6. Strong, flexible stems.
7. High production of flowering stems per plant with 6–8 flowering stems at first flush.
8. High production of flowers, with 5 to 6 flowering laterals eveloping per stem.
9. Flowering response of 26 to 30 weeks after planting rooted cuttings.
10. Very resistant to *Fusarium oxysporum.*
11. Recommended as a miniature (spray) carnation. The cultivar has not been trailed as a disbud or standard.

The accompanying photographic drawings show typical inflorescence of Adela, with the colors being as nearly true as possible with illustrations of this type. Sheet 1 is a color photograph of Adela grown as a spray cut carnation. Sheet 2 is a black and white photograph of three views of the inflorescence of Adela. In sheet 2, a measuring tape in centimeters has been added.

Of the commercial cultivars known to the inventor, the most similar in comparison to Adela is the unpatented cultivar identified as Bagatel, a white spray carnation. Similar traits are flower type and form, flower color, low to no incidence of calyx splitting, strong, flexible stems, production of stems per plant and production of flowers per stem, and recommendation as spray carnation. Adela has a larger flower diameter by 10 to 15 mm, and more petals per flower when compared with Bagatel. Adela has strongly serrated petals with shallow to intermediate serration of petal margins, while Bagatel has very slight serrated to almost smooth petal margins. Adela has very slight to no fragrance, while Bagatel has a very strong fragrance. Both cultivars are resistant to *Fusarium oxysporum.*

In the following description, color references are made to The Royal Horticultural Society Colour Chart. The color values were determined on plant material grown as spray carnations in Salinas, Calif. on Jun. 5, 1992.

Classification:

*Botanical.*—*Dianthus caryophyllus L.* cv Adela.

*Commercial.*—Spray carnation for cut flower production.

INFLORESCENCE

Form: Flat, high centered.

Type: Commercial double.

Flower diameter: 65 to 70 mm when fully opened.

Number of petals: 35 to 50 arrangement generally imbricated.

Color (general tonality from a distance of three meters): White. Color (upper surface: 155A color is solid and stable during maturity.

Shape: Rounded, slightly serrated with shallow to intermediate serration.

Androecium: Normal to semi-petaloid stamens; normal to degenerated anthers; moderate pollen.

Gynoecium: Typical carnation, smooth, conical ovaries.

Fragrance: None to very slight, typical carnation.

Fertility: No fertility level has been established.

Keeping quality: 7–14 days after cutting.

PLANT

A. General appearance:

*Growth.*—Bushy, semi-erect perennial; plant is normally pinched approximately 3 weeks after planting to produce upright habit typical of cut carnations. Rooting time for cuttings is 14–18 days year around at 68°–72° F.

*Branching.*—Semi-erect, numerous and unrestricted at base of plant; 5–6 flowering laterals developing per stem.

*Size.*—Two (2) year old plants may reach 150–200 cm in height.

*Stems.*—Cut stems range in length from 45 cm to 65 cm, and stems are round in cross-section.

B. Foliage:

*Color.*—Typical carnation, closest to 189A overlaid with 189B.

*Shape.*—Long, narrow, lancet shaped.

*Size.*—Mature leaves 9–11 cm in length and 6–7 mm in width; weakly curled.

*Texture.*—Surface has a thin wax-like finish which is bluish green in color.

C. Flowering: The first flush of flowers appears 26 to 30 weeks after planting rooted cuttings, and there are approximately 6–8 flowering stems at first flush when the apical bud is removed. The side laterals then grow out in approximately 8 weeks after which the second flush of flowers appears. The flowers of the first and second flushes are similar in size but in subsequent flowerings the flowers tend to become somewhat smaller. There are approximately 6–8 flushes of flowers during a two-year plant life at which time a commerical plant would typically be discarded.

I claim:

1. A new and distinct carnation plant named Adela, as described and illustrated.

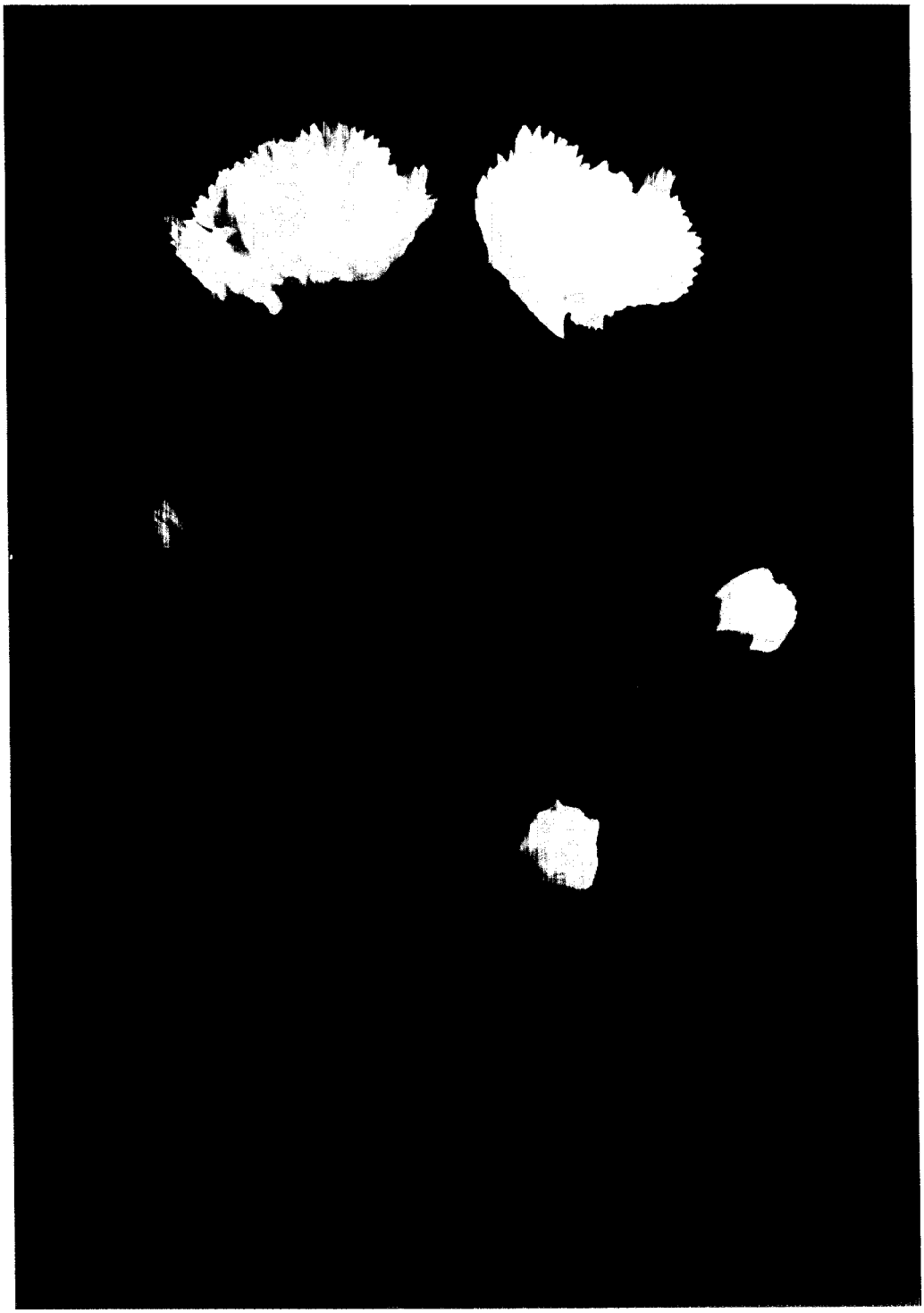

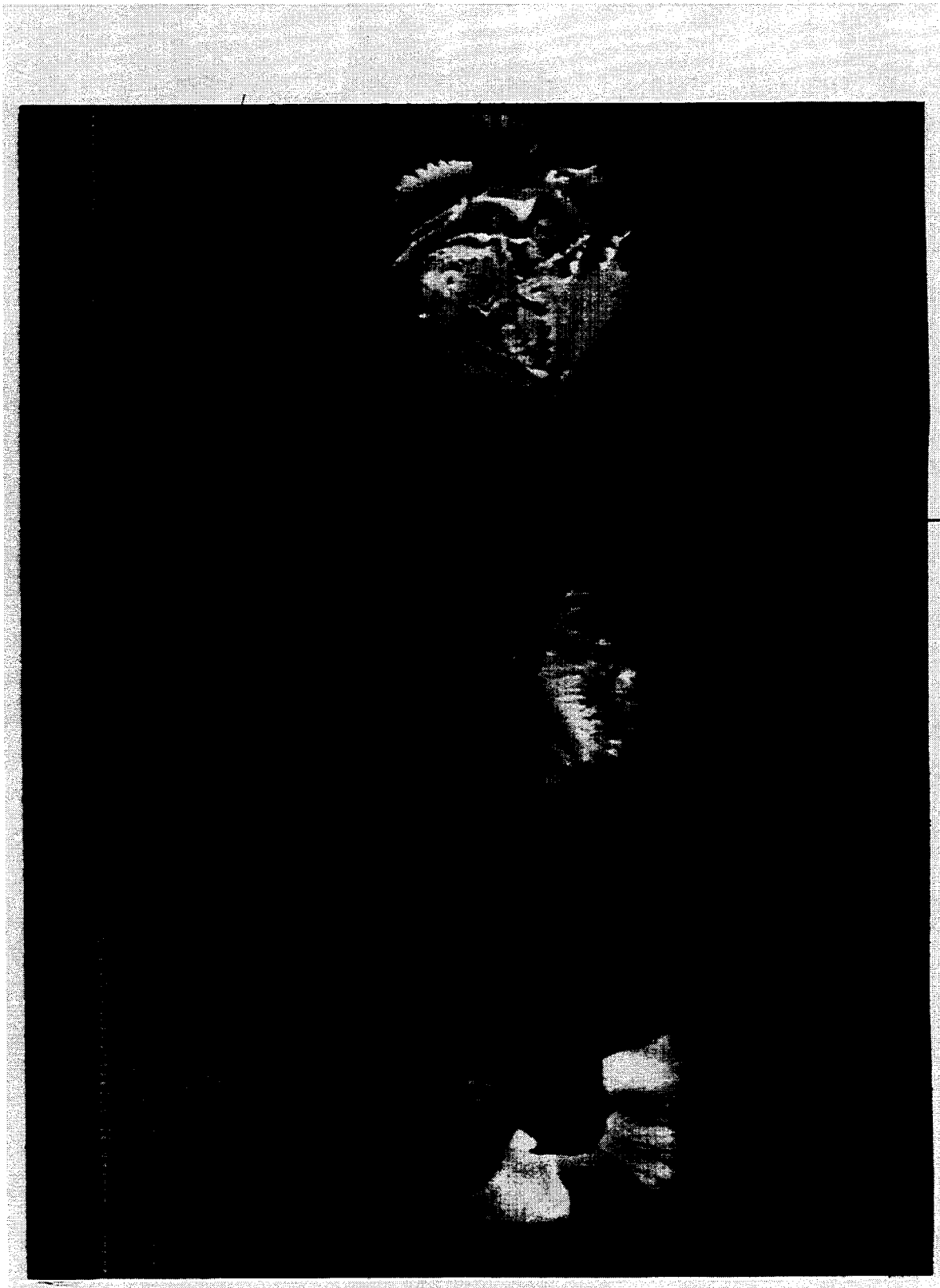

* * * * *